(12) United States Patent
Sugiyama

(10) Patent No.: US 7,824,865 B2
(45) Date of Patent: Nov. 2, 2010

(54) METHOD FOR EXAMINING WT1-RELATED DISEASE

(76) Inventor: Haruo Sugiyama, 2-19-30, Senbanishi, Mino-shi, Osaka (JP) 562-0036

( * ) Notice: Subject to any disclaimer, the term of this patent is extended or adjusted under 35 U.S.C. 154(b) by 721 days.

(21) Appl. No.: 11/037,128

(22) Filed: Jan. 19, 2005

(65) Prior Publication Data

US 2005/0148037 A1     Jul. 7, 2005

Related U.S. Application Data

(62) Division of application No. 10/276,918, filed as application No. PCT/JP01/04353 on May 24, 2001, now abandoned.

(30) Foreign Application Priority Data

May 24, 2000  (JP) .............................. 2000-152923
Jan. 23, 2001  (JP) .............................. 2001-014927

(51) Int. Cl.
*G01N 33/53* (2006.01)
(52) U.S. Cl. ...................... 435/7.1; 436/64; 436/500; 530/350; 530/387.1; 530/387.7; 530/387.9; 530/389.7
(58) Field of Classification Search .................. 436/64, 436/501; 435/7.1; 530/350, 387.1, 387.7, 530/387.9, 389.7
See application file for complete search history.

(56) References Cited

U.S. PATENT DOCUMENTS

| | | | |
|---|---|---|---|
| 5,633,142 A | 5/1997 | Herlyn et al. | |
| 6,225,051 B1 | 5/2001 | Sugiyama et al. | |
| 2003/0082194 A1 | 5/2003 | Gaiger et al. | |
| 2003/0082196 A1 | 5/2003 | Gaiger et al. | |
| 2003/0215458 A1* | 11/2003 | Gaiger et al. ............. | 424/185.1 |

FOREIGN PATENT DOCUMENTS

| WO | WO 97/39354 | 10/1997 |
|---|---|---|
| WO | 00/18795 A2 | 4/2000 |

OTHER PUBLICATIONS

Menssen H.D. et.al. Detection by monoclonal antibodies of the Wilm's tumor (WT1) nuclear protein in patients with acute leukemia. Int.j.Cancer. 70: 518-523, 1997.*
Gaiger A. et.al. Immunity to WT1 in the animal model and in patients with acute myeloid leukemia. Blood. 96: 1480-1489, 2000.*
Siehl et al. (Ann. Hematol. 2004; 83: 745-750).*
Zolg et al. (Mol. Cell. Prot. 2004; 3 (4): 345-354).*
Call et al. (Cell. Feb. 9, 1990; 60: 509-520).*
Gessler et al. (Nature. Feb. 22, 1990; 343 (6260): 774-778).*
Inoue et al. (Blood. Apr. 15, 1998; 91 (8): 2969-2976).*
Lacroix et al. (Sem. Surg. Oncol. 2001; 20: 252-264).*
Tsavellas et al. (Br. J. Surg. Oct. 2001; 88 (10): 1307-1320).*
Leifers et al. (Histopathology. May 1999; 34 (5): 385-390.*
Calaluce et al. (J. Surg. Oncol. 1998; 67: 194-202).*
Miyamura et al. (Int. J. Hematol. 2004; 79: 243-249).*
Elisseeva, O.A., "Humoral immune responses against Wilms' tumor gene WT1 product in patients with hematopoietic matlignancies," *Osaka Daigaku Igaku Zassi*, Osaka Univ. Society, Jan. 2001, vol. 52, pp. 63-72.
Inoue, K. et al., "WT1 as a new prognostic factor and a new marker for the detection of minimal residual disease in acute leukemia," *Blood*, Nov. 1, 1994, vol. 84, pp. 3071-3079.
Tamaki, H. et al., "The Wilms' tumor gene WT1 is a good marker for diagnosis of disease progression of myelodysplastic syndromes," *Leukemia*, 1999, vol. 13, pp. 393-399.
Volinelich, L. et al., "A monoclonal antibody (WT1) for detecting leukemias of T-cells precursors (T-ALL)," *Blood*, Nov. 1983, vol. 62, pp. 1108-1113.
Gaiger, A., et al., "WT-1 specific serum antibodies in patients with leukemia," *Clinical Cancer Research*, Mar. 2001, vol. 7, pp. 761-765.
Gaiger, A., et al., "Immunity to WT1 in the animal model and in patients with acute myeloid leukemia," *Blood*, Aug. 15, 2000, vol. 96, pp. 1480-1489.
Elisseeva, O.A. et al., "Humoral immune responses against Wilms tumor gene WT1 product in patients with hematopoietic malignancies," *Blood*, May 1, 2002, vol. 99, pp. 3272-3279.
Gaiger et al, *Blood*, 94 (10, Suppl. 1, part I):78a(1999).
Haruo Sugiyama, "Hakketsu byou no Idenshi Shindan: WT1 ni yoru Saihatsu, Kankai, Hasshou Yosoku" *Rinshou Byouri* (Feb. 2000), vol. 48, No. 2, pp. 155-161.
Olga A. Elisseeva, "Zouketsuki Akusei Shikkan Kanja ni okeru Wilms' tumor Idenshi (WT1) Sanbutsu no taisuru Ekisei Meneki Hannou", *Osada Daigaku Igaku Zasshi* (Jan. 2001, vol. 52, No. 12, Separate vol. 2, pp. 63-72.
Gaiger et al, Clin Cancer REs. Mar. 2001; 7 (3 Suppl): 761s-765s.
Ladomery M, et al., J Cell Sci. 2003; 116; 1539-49.
Loeb, DM et al Leukemia May 2003; 17 (5): 965-71.
Dumur CI, et al, Anal Biochem, Oct. 1, 2002; 309 (1); 127-36.
Ward AM Developmental Oncol. 1985; 21; 90-106.
Tockman MS, et al., Cancer Res. 1992; 52 (Suppl.): 2711s-2718s.
Gaiger et al, *Blood*, Aug. 15, 2000, vol. 96, No. 4.
Surinder S. Sahota et al., "$V_H$ Gene Analysis of Clonally Related IgM and IgG From Human Lymphoplasmacytoid B-Cell Tumors With Chronic Lymphocytic Leukemia Features and High Serum Monoclonal IgG", Blood, 1998, 91(1): 238-243.
M. Wakai et al., "IgG+, CD5+ human chronic lymphocytic leukemia B cells. Production of IgG antibodies that exhibit diminished autoreactivity and IgG subclass skewing", Autoimmunity, 1994, 19(1): 39-48.
Franco Fais et al., "Examples of In Vivo Isotype Class Switching in IgM+ Chronic Lymphocytic Leukemia B Cells", Journal of Clinical Investigation, 1996, 98(7):1659-1666.

\* cited by examiner

*Primary Examiner*—Stephen L Rawlings
(74) *Attorney, Agent, or Firm*—Sughrue Mion, PLLC

(57) ABSTRACT

The invention provides a method for testing a WT1-related disease, such as leukemia, a solid cancer, or an atypia, for diagnosing the disease, evaluating the course of cure and the prognosis of the disease more simply with high reliability, the method comprises measuring the amount of antibody against WT1 in a sample and using the measurement value and the time course of the value as a clinical marker for the testing.

4 Claims, 11 Drawing Sheets

METHOD FOR EXAMINING WT1-RELATED DISEASE

This is a divisional of application Ser. No. 10/276,918 filed Nov. 22, 2002 now abandoned, which is a 371 of PCT/JP01/04353 filed May 24, 2001.

TECHNICAL FIELD

This invention relates to an examination method for WT1-related disease and more particularly to a method of testing for the presence of such a disease and of evaluating the progression, course of cure, and prognosis of the disease.

BACKGROUND ART

WT1 gene is a zinc finger transcription factor isolated as a gene etiologically associated with Wilms' tumor and its gene product (WT1 protein) has a structure comprising a repression domain, an activation domain, and a zinc finger.

The inventors previously reported that the expression level of WT1 gene is high in acute leukemia, that this expression level is inversely correlated with the prognosis of the disease, and that the MRD (minimal residual disease) of acute leukemia can be detected by measuring said expression level [Blood, Vol. 84, No. 9, p 3071 (1994)]. Furthermore, the inventors found that by measuring the expression level of WT1 gene, various types of solid cancer and tissue atypia can be detected (WO97/39354).

Determination of said expression level of WT1 gene which comprises measuring the transcription or translation product of WT1 gene has a great clinical significance in a search for the presence of a WT1 related disease.

DISCLOSURE OF INVENTION

The object of the present invention is to provide a novel method for examining a WT1-related disease, particularly an effective method for diagnosing the disease and evaluating the efficacy of a therapy and the prognosis of the disease.

In the course of their continuing research for accomplishing the above object, the inventors discovered that the amounts of the anti-WT1 antibody detected in serum or other test specimens from patients with WT1-related disease decline with the healing of the disease, so that the amount of anti-WT1 antibody can be a novel clinical marker of WT1-related disease, and that by measuring said amount the presence of a WT1-related disease can be detected, as well as the progression, course of cure, and prognosis of the disease can be monitored and assessed with high reliability.

The present invention has been developed on the basis of the above findings.

The invention provides a method of testing a WT1-related disease which comprises measuring the amount of antibody against WT1 in a sample and using the measurement value as a clinical marker or index for the testing.

In particular, the invention provides the following modes of testing for WT1-related disease.

1. A method which comprises detecting the presence of a WT1-related disease.
2. A method for assessing the progression, course of cure, and prognosis of a WT1-related disease.
3. A method for monitoring the progression of myelodysplastic syndrome to leukemia.
4. A method for ascertaining a complete remission of leukemia.
5. A method which comprises assaying anti-WT1 antibody by an immunoreaction using a WT1 antigen.
6. A method as defined above wherein the WT1 antigen is a WT1 protein containing a repression domain and an activation domain but lacks a zinc finger.
7. A method as defined above wherein the anti-WT1 antibody is an IgG antibody or an IgM antibody.
8. A method which comprises using the time course of the amount of anti-WT1 antibody method as a clinical marker.
9. A method which comprises using the quantitative ratio of the IgG antibody and IgM antibody against WT1 as a clinical marker.

The representation of amino acids, peptides, nucleotide sequences, nucleic acids, etc. by abbreviations in this specification invariably conforms to the rules of IUPAC-IUB, "the Guidelines for Drafting Specifications and Equivalents referring to Nucleotide Sequences or Amino Acid Sequences" (ed. by The Patent Office of Japan), and the conventions prevailing in this particular field of art.

The method of testing for WT1-related disease according to the invention is carried into practice by measuring the amount of anti-WT1 antibody in a sample.

The sample mentioned above is not restricted provided that it harbors an anti-WT1 antibody. The sample may be a sample derived from a patient with WT1-related disease or a patient suspected to have the disease and a sample derived from a patient who was once on the treatment of a WT1-related disease. The sample may be a body fluid in which antibodies are generally known to occur, such as blood, urine or the like.

Referring to the WT1-related disease to be tested for presence in accordance with the invention, various WT1-related diseases such as said acute leukemia and other types of leukemia, solid cancer, atypia, etc. can be exemplified.

The anti-WT1 antibody to be assayed in accordance with the invention is an antibody to the expression product (WT1 protein) of WT1 gene [Cell, 60, 509 (1990); Nature, 343, 774 (1990)]. This includes all the relevant antibodies detected in a subject. The antibody as such includes various immunoglobulins such as the IgG antibody, IgA antibody and IgM antibody.

The assay of the anti-WT1 antibody according to the invention can be carried out by the various techniques in routine use in the art of antibody determination, such as an immunoassay method using a WT1 antigen, among others. A specific example of the immunoassay method is a solid-phase sandwich technique.

This solid-phase sandwich technique can be carried out typically in the following manner. Thus, an antigen (WT1 antigen) capable of undergoing a specific antigen-antibody reaction with the objective antibody against WT1 (anti-WT1 antibody) is first immobilized and a sample is added thereto. Thereupon, an antigen-antibody reaction takes place between the immobilized antigen and the antibody occurring in the sample so that the anti-WT1 antibody present in the sample is bound to the immobilized antigen. Then, this bound antibody is detected with an antibody detecting reagent, whereby the anti-WT1 antibody occurring in the sample can be assayed.

This solid-phase sandwich technique can be carried out in the following alternative manner. Thus, the antibody detecting reagent is immobilized in the first place and caused to capture the antibodies occurring in the sample and the WT1 antigen is then added thereto and caused to bind the anti-WT1 antibody among the captured antibodies. Further, a labeled antibody obtained by labeling the specific antibody against said antigen is caused to couple with said antigen to thereby detect and determine the objective anti-WT1 antibody occurring in the sample.

Selection of various means and modification thereof in these assay techniques are invariably well known to those skilled in the art and any of such means and versions can be utilized substantially without restriction in the practice of the present invention [cf. Rinsho Kensaho Teiyo (Clinical Laboratory Test Protocols), Kanehara Publishing Co., 1995, for instance].

Regarding the antibody detecting reagent to be utilized as above, a variety of reagents which are in routine use for detecting various immunoglobulins such as IgG can be employed without restriction. Examples of such reagents include the anti-human IgG antibody, anti-human IgM antibody, and anti-human Ig(G+M) antibody which binds specifically to the human IgG, human IgM, or both, which is to be determined, and a preparation thereof. These can be purchased from commercial sources or optionally prepared by per se established procedures.

The WT1 antigen to be utilized as above may be any antigen that is specific to the WT1 gene product (protein). This antigen may be a WT1 protein as such or its fragment having a WT1 protein-specific epitope. The WT1 antigen mentioned above includes the antigen chemically synthesized in accordance with the amino acid sequence information on the WT1 protein or the antigen prepared by a genetic engineering technique. It is to be understood that whether a candidate WT1 antigen can be used satisfactorily in the practice of the invention can be easily ascertained, for example by carrying out an antigen-antibody reaction in the routine manner using an antibody which has been established to be the WT1 antibody harbored by a patient with WT1-related disease.

In the present invention, the WT1 antigen which is particularly suited as the assay system antigen is one containing the repression domain and activation domain of WT1 protein and yet being defect of a zinc finger. Among species thereof, a protein (hereinafter referred to briefly as HWT3) having a partial sequence consisting in the 1~294-residue portion of the amino acid sequence of WT1 protein is particularly preferred. The HWT3 can be produced by a genetic engineering technique using the known WT1 gene, for example by the method described as a specific example in the Best Mode section presented hereinafter or any method analogous thereto.

Production of a WT1 antigen by a genetic engineering technique utilizing WT1 gene can be carried out in accordance with the hitherto-known general recombinant gene technology. More particularly by the method comprising constructing a recombinant DNA such that the WT1 gene of interest can be expressed in host cells, transfecting host cells therewith, and growing the resulting transformant, the objective WT1 antigen can be produced as a gene expression product intracellularly or extracellularly of the transformant.

The various operations and manipulations which can be used in the above production of WT1 antigen, such as the chemical synthesis, enzymatic treatment for cleavage, deletion, addition and ligation of a gene or its fragments, isolation, purification, selection, etc., introduction of the recombinant DNA into host cells, and culture of the transformant cells, among others, can all be carried out in accordance with established procedures [cf. "Bunshi Idengaku Jikkenho (Experimental Protocols in Molecular Genetics), Kyoritsu Publishing Co., 1993; PCR Technology, Takara Shuzo Co., 1990; Science, 224, 1431 (1984); Biochem. Biophys. Res. Comm., 130, 692 (1985); Proc. Natl. Acad. Sci., USA, 80, 5990 (1983); Moplecular Cloning, by T. Maniatis et al., Cold Spring Harbor Laboratory (1982), etc.].

If desired, the WT1 antigen can be isolated and purified from the above-mentioned expression product or the like in accordance with various separatory techniques utilizing its physical and/or chemical properties [e.g. "Biochemistry Data Book II, pp. 1175-1259, First Edition, 1st impression, Jun. 23, 1980, published by K. K. Tokyo Kagaku Dojin, etc.].

Determination of the amount of anti-WT1 antibody in a sample according to the invention can also be carried out by utilizing various assay systems using known techniques and means. In such assay systems, the hitherto-known assay reagents, for instance, can be used with advantage.

Taking an assay system using a solid-phase technique as an example, either the antigen or the antibody is immobilized on a solid phase in the routine manner. As the solid phase, the insoluble and inert carriers or supports can be liberally employed. Examples of the carriers or supports are sticks, beads, microplates, test tubes, etc. made of various materials, such as glass, cellulose powder, Sephadex™, Sepharose™, polystyrene, filter paper, carboxymethylcelulose, ion exchange resin, dextran, plastic film, plastic tube, polyamide resin, glass beads, silk, polyamine-methyl vinyl ether-maleic acid copolymer, amino acid copolymer, ethylene-maleic acid copolymer, and so on.

Immobilization of the antigen or the antibody can also be carried out by the known technology substantially without restriction. This technology includes the methods depending on physical bonding, those depending on chemical bonding, and those utilizing both. Typical examples are various methods utilizing chemical coupling reactions such as covalent bonding, e.g. diazo method, peptide method (acid amide derivative method, carboxyl chloride resin method, carbodiimide resin method, maleic anhydride derivative method, isocyanate derivative method, cyanogen bromide-activated polysaccharide method, cellulose carbonate derivative method, condensation reagent method, etc.), alkylation method, support-binding method using a crosslinking reagent (glutaraldehyde, hexamethylene isocyanate, or the like is used as the crosslinking agent), the carrier binding method using a Ugi reaction, etc.; the ion bonding method using an ion exchange resin or the like carrier; and the physical adsorption method using a porous glass, such as glass beads, as the carrier.

The labeling agent for use in each assay system is not particularly restricted but may be any of the hitherto-known agents. Specific examples include the various radioisotopes which are conventionally used in immunoassays; enzymes such as alkaline phosphatase (ALP), peroxidase (POX), etc.; fluorescent substances such as fluorescein isothiocyanate (FITC), tetramethylrhodamine isothiocyanate (RITC), etc.; and others, for example 1N-(2,2,6,6-tetramethyl-1-oxyl-4-piperidyl)-5N-(aspartate)-2,4-dinitrobenzene (TOPA).

As the enzymes for enzymatic labeling, not only the above-mentioned substances but also microperoxidase, chymotrypsinogen, procarboxypeptidase, glyceroaldehyde-3-phosphoric dehydrogenase, amylase, phosphorylase, D-nase, P-nase, etc. can be employed. The labeling with such a labeling agent can be carried out by the known technology [cf. Tatsuo Iwasaki et al.: Monoclonal Antibody, Kodansha Scientific, 1984; Eiji Ishikawa et al.: Enzyme Immunoassay, 2nd ed., Igaku Shoin, 1982; etc.].

Determination of enzyme activity can also be carried out in the known manner according to the kind of enzyme used. For example, said determination can be made by using ABTSJ (2,2'-azino-bi(3'-ethylbenzothiazoline-sulfonic acid) as the substrate when a peroxidaze is used as the labeling agent or p-nitrophenyl phosphate as the substrate when alkaline phosphatase is used as the labeling agent and measuring the decomposition of the substrate with a spectrophotometer or the like [cf. Eiji Ishikawa et al.: Enzyme Immunoassay, 2nd ed., Igakushoin, 1982, for instance].

When a radioisotope or a fluorescent substance is used in lieu of said enzyme as the label, determination of the labeled immunoglobulin can be carried out by the known technique utilizing the particular label.

The solvent for use in each assay system may be any solvent that does not adversely affect the reaction in the particular assay system. Examples of preferred solvents for general use are buffer solutions having pH values within the range of about pH 5-9, such as citrate buffer solution, phosphate buffer solution, Tris-HCl buffer solution, acetate buffer solution, and so on.

The conditions of the immune reaction (binding) are not particularly restricted, either. Thus, conditions in routine use for immunoassays of this kind can be utilized. Generally speaking, the reaction temperature is not over about 45° C., preferably in the range of about 4-40° C., and the reaction time is about 1-40 hours.

The most important feature of the invention is to utilize the amount of anti-WT1 antibody in a sample as a clinical marker of WT1-related disease.

Compared with healthy subjects, the level of anti-WT1 antibody in a patient with WT1-related disease is significantly elevated and declines with the progress of cure of the disease. Therefore, by taking this level of anti-WT1 antibody and its change, particularly the time course of the amount of anti-WT1 antibody, as a clinical marker, the presence of a WT1-related disease, the course of cure, and prognosis can be estimated. A decrease in the amount of anti-WT1 antibody in a sample can be regarded as a particularly desirable clinical marker.

The inventors found that, among said various anti-WT1 antibodies, the amounts of IgM anti-WT1 antibody and IgG anti-WT1 antibody, the respective time courses, and the time course of their ratio serve as more effective markers of the presence, course of cure, and prognosis of a WT1-related disease.

Furthermore, the inventors confirmed that in WT1-related disease, particularly myelodysplastic syndrome (MDS), there occurs a class switch of WT1 antibody from IgM to IgG in association with the progression of illness. Therefore, by tracking the time course of the presence ratio of IgM anti-WT1 antibody versus IgG anti-WT1 antibody, it is possible to monitor the progression of illness in said MDS, that is to say the course of progression from refractory anemia (RA) through RA with excess of blasts to RAEB in transformation (RAEB-t) and further to leukemia.

The inventors further found that the anti-WT1 antibody disappears on complete remission of a WT1-related disease such as leukemia and that, therefore, the time interval in which this disappearance of the antibody persists can be regarded as the time period during which the above state of complete remission is sustained.

Detection of an anti-WT1 antibody in a patient with WT1-related disease, that is to say confirmation of an anti-WT1 antibody-positive patient, provides evidence that the patient is presenting with a humoral immune response to WT1. Therefore, the very detection of an anti-WT1 antibody is useful for the evaluation or diagnosis of the immunological competence of the patient. Compared with a patient not presenting with an immune response, a patient presenting with the same has higher immunity and may have an as much better prognosis. Therefore, determination of anti-WT1 antibody in a patient with WT1-related disease is of great use in diagnosing the immunological competence against the WT1-related disease, particularly (against cancer) in various cancer patients.

The examination method of the invention can be expediently carried out by utilizing a testing agent, preferably a test kit (test reagent). The present invention further provides a test reagent for ascertaining the presence, course of cure, and prognosis of a WT1-related disease.

The test reagent of the invention comprises a WT1 antigen, that is to say an antigen capable of undergoing an antigen-antibody reaction with the anti-WT1 antibody to be assayed, as an active ingredient. This test reagent may further comprises an optional reagent such as an antigen-detecting agent useful for the particular assay system. In addition, it may contain suitable reagents aiding in the determination process, such as an antibody diluent, a reaction diluent, a buffer, a wash solution, and a labeled activity detecting agent, among others.

BEST MODE FOR CARRYING OUT THE INVENTION

The following examples illustrate the invention in further detail. It should, however, be understood that these are not definitive of the scope of the invention.

Example 1

Determination of Anti-WT1 Antibody (1) Production of a WT1 Antigen

The WT1 gene (Blood, Vol. 91, p. 2969 (1998)) was integrated into the plasmid pBluescript II (product of Stratagene) and using this pBluescript II/WT1 (+/+) as the template, the DNA fragment was amplified by a PCR using a primer prepared by adding an EcoR I recognition sequence at the 5'-end (SEQ ID NO:1) and a primer prepared by adding a Not I recognition sequence at the 3'-end (SEQ ID NO:2). The amplified DNA fragment corresponds to a part of the WT1 gene cDNA coding for the sequence of $1^{st}$ to $294^{th}$ amino acids of WT1 protein.

Then, the DNA fragment thus obtained was ligated into a pGEX-5X-3 (Amersham Pharmacia Biotech) and used to transfect Escherichia coli BL 21 (DE3). For enhanced solubility of the fusion protein, the cells were simultaneously transfected with the thioredoxin expression plasmid pT-Trx. The E. coli was cultured overnight and the culture fluid was diluted 10-fold and incubated at 37° C. for 1.5 hours, at the end of which time isopropyl-β-D-thiogalactopyranoside (IPTG) was added at a final concentration of 0.1 mM, further followed by 5 hours' incubation. The cells were then recovered and, after addition of a cytolytic solution [50 mM Tris-HCl (pH 7.5), 50 mM NaCl, 1 mM EDTA, 1 mM Prefabloc SC (Boehringer Mannheim), 10 µg/ml leupeptin, 1 mM DTT], sonicated and centrifuged and the supernatant was recovered. The fusion protein in the supernatant was conjugated to glutathione-Sepharose 4B™ (Amersham Pharmacia Biotech), which was then washed, and the fusion protein was eluted with an elution buffer (50 mM Tris-HCl (pH 7.5), 150 mM NaCl, 20 mM reduced glutathione, 1 mM DTT) to recover GST-WT1 fusion protein HWT3.

Similarly, as described below, HWT2 (the WT1cDNA fragment coding for the sequence of $1^{st}$ to $181^{st}$ amino acids of WT1 protein) and HWT4 (the WT1cDNA fragment coding for the sequence of $182^{nd}$ to $294^{th}$ amino acids of WT1 protein) were produced.

Thus, with pBluescript II/WT1(+/+) as the template, a PCR was carried out using a primer containing an EcoRI recognition sequence at 5'-end and a primer containing a NotI recognition sequence at 3'-end (the 5'-primer having the sequence of SEQ ID NO:1 and the 3'-primer having the sequence of SEQ ID NO:3 for HWT2 or the 5'-primer having the sequence of SEQ ID NO:4 and the 3'-primer having the sequence of SEQ ID NO:2 for HWT4) to amplify the objective DNA fragment. Each DNA thus obtained was cloned into pGEX-5X-3 (Amersham Pharmacia Biotech) and used to transfect Escherichia coli BL21 (DE3). From this E. coli, WT1 fusion protein HWT2 or HWT4 was recovered in the same manner as described above.

Figure 1:
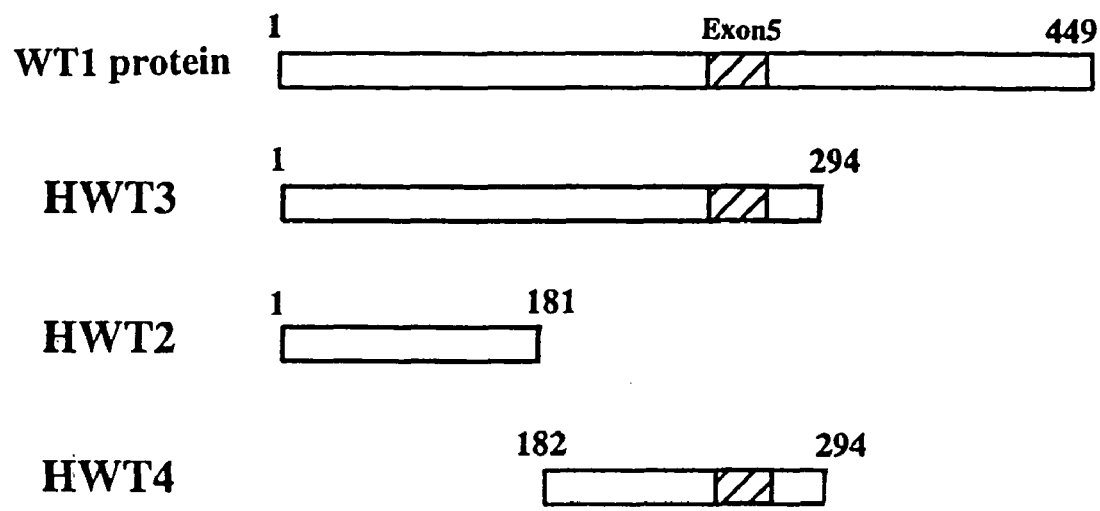
FIG. 1 is a schematic view illustrating the structures of the WT1 antigens produced in accordance with Example 1-(1).

The structures of the respective HWT2, HWT3 and HWT4 proteins obtained as above are schematically shown in comparison with WT1 in FIG. 1.

In FIG. 1, the 1-181 region represents a repression domain, the 182-294 region represents an activation domain, with a zinc finger following.

(2) A Test for Reactivity between WT1 Antigen and WT1 Antibody

The reactivity between the WT1 antigen and WT1 antibody constructed as above under (1) was tested as follows.

Thus, the GST fusion protein was dissolved in PBS at a concentration of 250 µg/ml and adsorbed on a nitrocellulose membrane (OPTITRAN, Schleicher & Schuell) at a concentration of 25 µg/cm$^2$. This nitrocellulose membrane was washed with PBS, immersed in 2% bovine serum albumin (BSA) solution for 2 hours, and mounted on a dot-blot apparatus (Schleicher & Schuell). On the nitrocellulose membrane carrying the GST fusion protein adsorbed, 20 µl of anti-WT1 antibody solution was placed and reacted for 1 hour, and after washing with PBS, the membrane was further reacted with the HRP-conjugated anti-IgG antibody for 1 hour. After washing, the membrane was immersed in a substrate solution (RENAISSANCER, NEN Life Science Products) for reaction, and after drying, the membrane was held in contact with photosensitive film (HYPERFILM MP, Amersham Life Science). After exposure of the film, the density of the band on the film was measured with a computerizable scanning analysis system (Molecular Dynamics) to calculate the antibody titer in densitometric units.

The anti-WT1 antibodies used are as follows.

S-Cruz 180: A rabbit polyclonal antibody against the GST fusion protein containing the N-terminal 180-residue sequence of human WT1 (product of Santa Cruz Biotechnology, Inc.)

Pharmingen: A mouse anti-human WT1 protein monoclonal antibody recognizing the exon 5 sequence as obtained by immunizing a synthetic peptide corresponding to the exon 5 sequence of human WT1 (product of Pharmingen).

(3) Results

Figure 2:
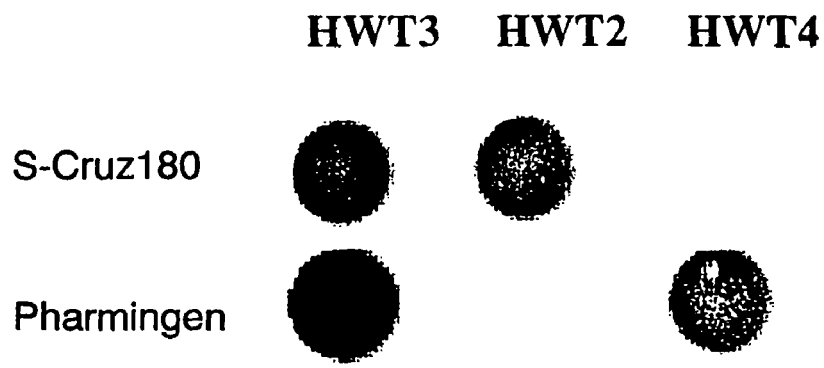
FIG. 2 is a view showing the results of the test for reactivity between WT1 antigen and anti-WT1 antibody in accordance with Example 1-(2).

The results are presented in FIG. 2.

The following can be deduced from the results shown in FIG. 2. Thus, whereas HWT2 reacts exclusively with the rabbit polyclonal antibody S-Cruz 180 and HWT4 reacts exclusively with the mouse monoclonal antibody Pharmingen, HWT3 was found to react with both.

For the broad-range detection of anti-WT1 antibodies in a sample; HWT3 was used as the antigen for detecting anti-WT1 antibodies in the following procedure.

Example 2

Test 1 for WT1-Related Disease (1) Preparation of a Sample

The test serum was diluted 2500-fold with PBS containing 2% of BSA and 0.05% of Tween™ 20 to prepare a sample.

(2) Preparation of the Antigen-Adsorbed Membrane

The HWT3 fusion protein solution (250 µg/ml) was placed and allowed to be adsorbed on a nitrocellulose membrane (OPTITRAN, Schleicher & Schuell) at a concentration of 25 µg/cm$^2$ for 1 hour. This membrane was washed with PBS, then immersed in blocking solution (2% bovine serum albumin solution) for 2 hours, washed, and used as the antigen-adsorbed membrane.

(3) Determination of WT1 Antibody

Using the antigen-adsorbed membrane obtained as above under (2), each of the anti-WT1 antibodies (IgG and IgM) contained in the sample prepared under (1) was determined in the same manner as described in Example 1-(2).

Thus, the nitrocellulose membrane supporting the GST fusion protein as adsorbed thereon was mounted on a dot-blot apparatus and 20 µl of the sample (diluted serum) was placed on the membrane and incubated for 1 hour. After washing with PBS, the membrane was further reacted, in 1% BSA/PBS, with the HRP-conjugated goat anti-human IgM antibody (ICN Pharmaceuticals Inc.) in the case of IgM antibody for 1 hour. In the case of IgG antibody, it was further reacted with HRP-conjugated rabbit anti-human IgG antibody (ICN Pharmaceuticals Inc.) for 1 hour. After completion of the reaction, the membrane was washed with PBS, immersed in substrate solution for reaction, dried, and placed in intimate contact with photosensitive film. The film was then exposed and the density of the band on the film was measured to find the antibody titer (in densitometric units). These procedure were invariably carried out at room temperature.

(4) Assay Results (a) The results obtained using samples from 43 healthy adult volunteers and 33 patients with WT1-related disease (12 with myelodysplastic syndrome (MDS), 12 with acute myelocytic leukemia (AML), 4 with acute lymphocytic leukemia (ALL), and 5 with chronic myelocytic leukemia (CML)) in accordance with the above-described method are presented in FIGS. 3-6.

On each view, the ordinate represents antibody titer (densitometric units) and the abscissa represents each sample.

Figure 3:
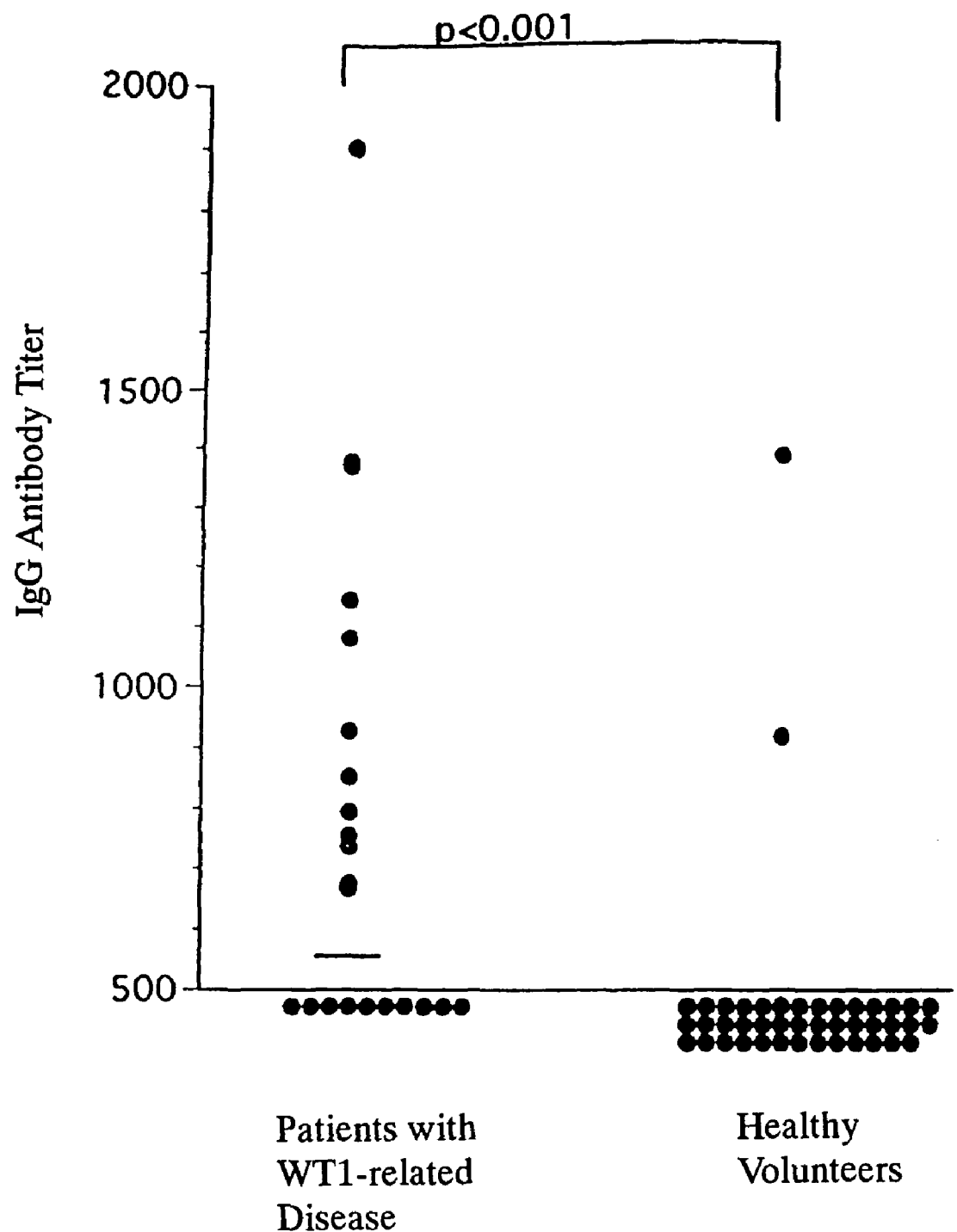
FIG. 3 is a graph showing anti-WT1 antibody titers (IgG) in WT1-related disease patients and healthy volunteers as determined by the examination method of the invention in Example 2.

The results presented in FIG. 3 indicate that compared with healthy volunteers, patients with WT1-related disease have significantly ($p<0.001$) high IgG anti-WT1 antibody titers.

Figure 4:
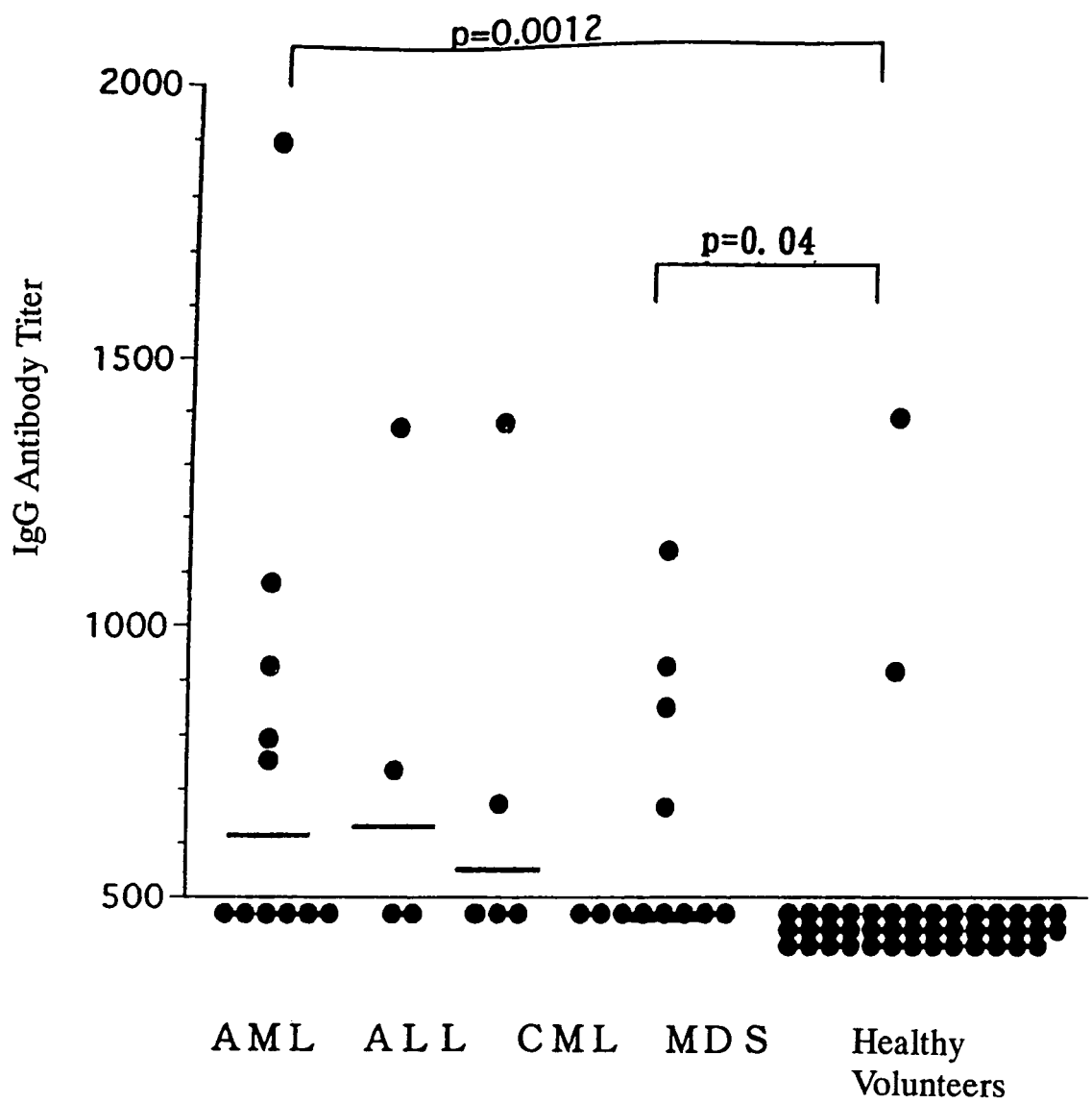
FIG. 4 is a graph showing anti-WT1 antibody titers (IgG) in WT1-related disease patients and healthy volunteers as determined by the examination method of the invention in Example 2.

The results presented in FIG. 4 indicate that compared with healthy volunteers, patients with AML and those with MDS have significantly high IgG anti-WT1 antibody titers.

Figure 5:
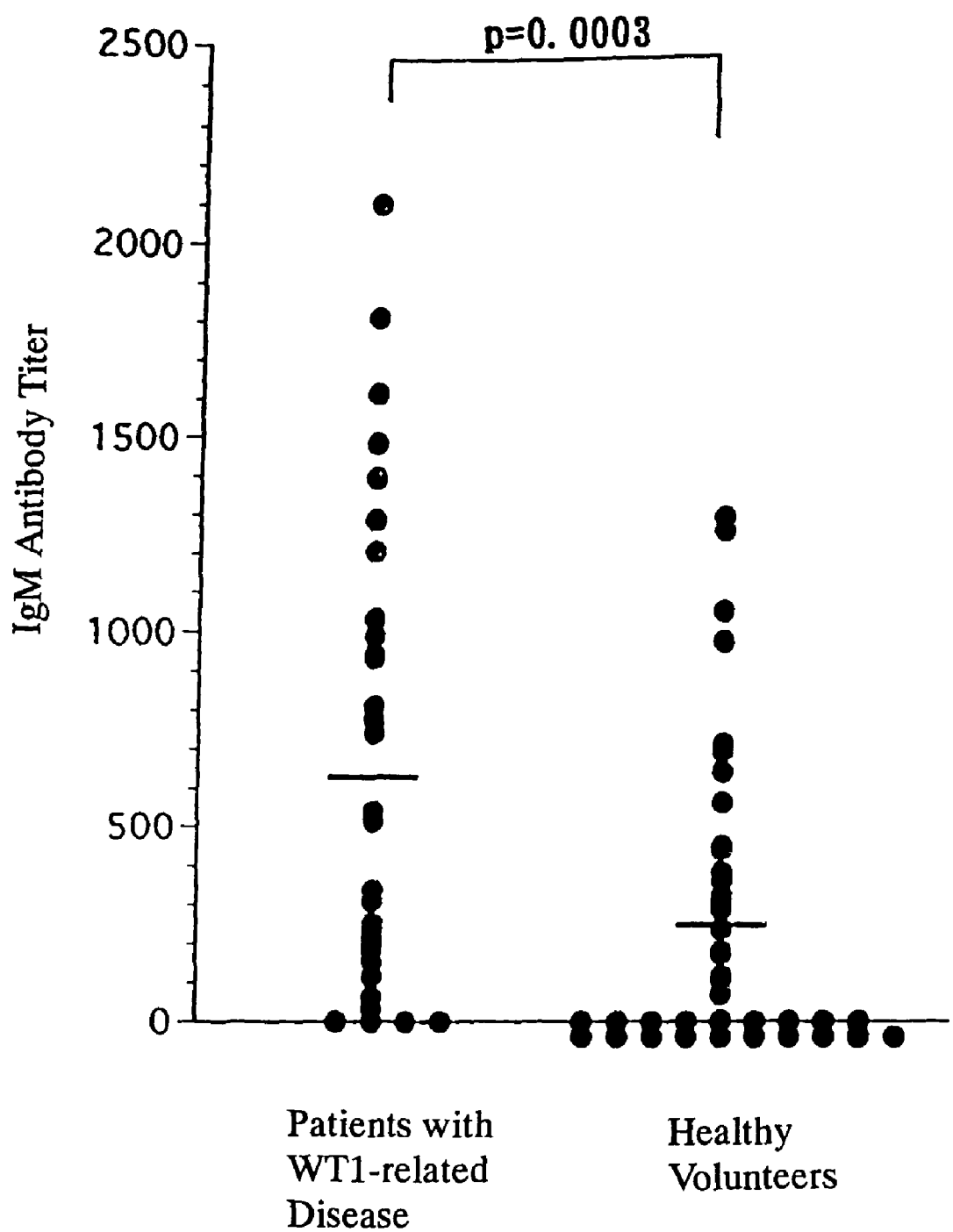
FIG. 5 is a graph showing anti-WT1 antibody titers (IgM) in WT1-related disease patients and healthy volunteers as determined by the examination method of the invention in Example 2.

The results presented in FIG. 5 indicate that compared with healthy volunteers, patients with WT1-related disease have significantly ($p=0.0003$) high IgM anti-WT1 antibody titers.

Figure 6:
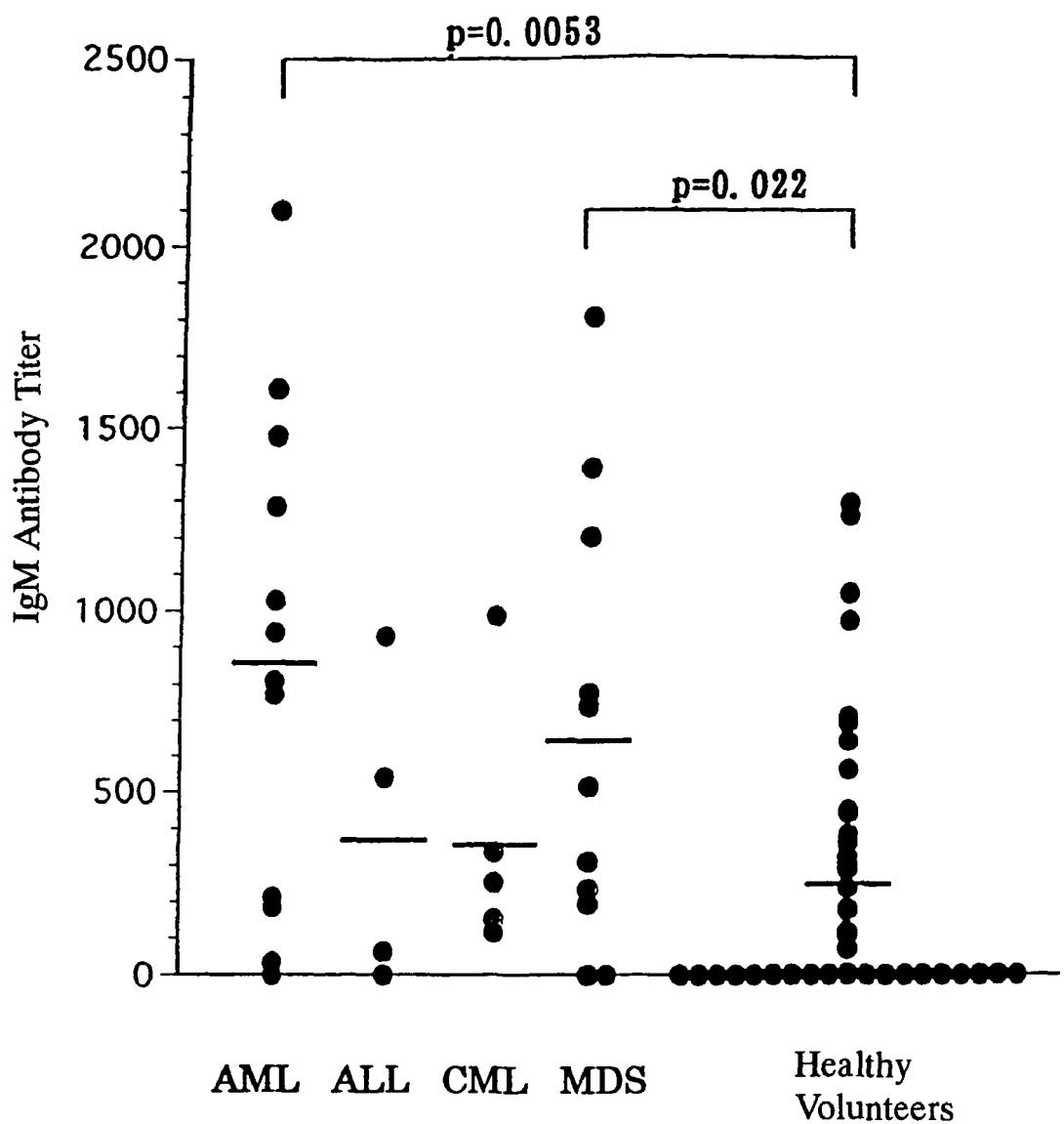
FIG. 6 is a graph showing anti-WT1 antibody titers (IgM) in WT1-related disease patients and healthy volunteers as determined by the examination method of the invention in Example 2.

The results presented in FIG. 6 indicate that compared with healthy volunteers, patients with AML and those with MDS have significantly high IgM anti-WT1 antibody titers.

These findings are evidence that by determining the IgG and/or IgM anti-WT1 antibodies, it is possible to diagnose the presence of WT1-related diseases such as AML, ALL, CML, and MDS.

Example 3

Test for Prognosis in Patients with WT1-Related Disease

In the same manner as described in Example 2, the IgG anti-WT1 antibody titer was measured in 6 acute leukemia patients before treatment and after treatment (on complete remission (CR)).

Figure 7:
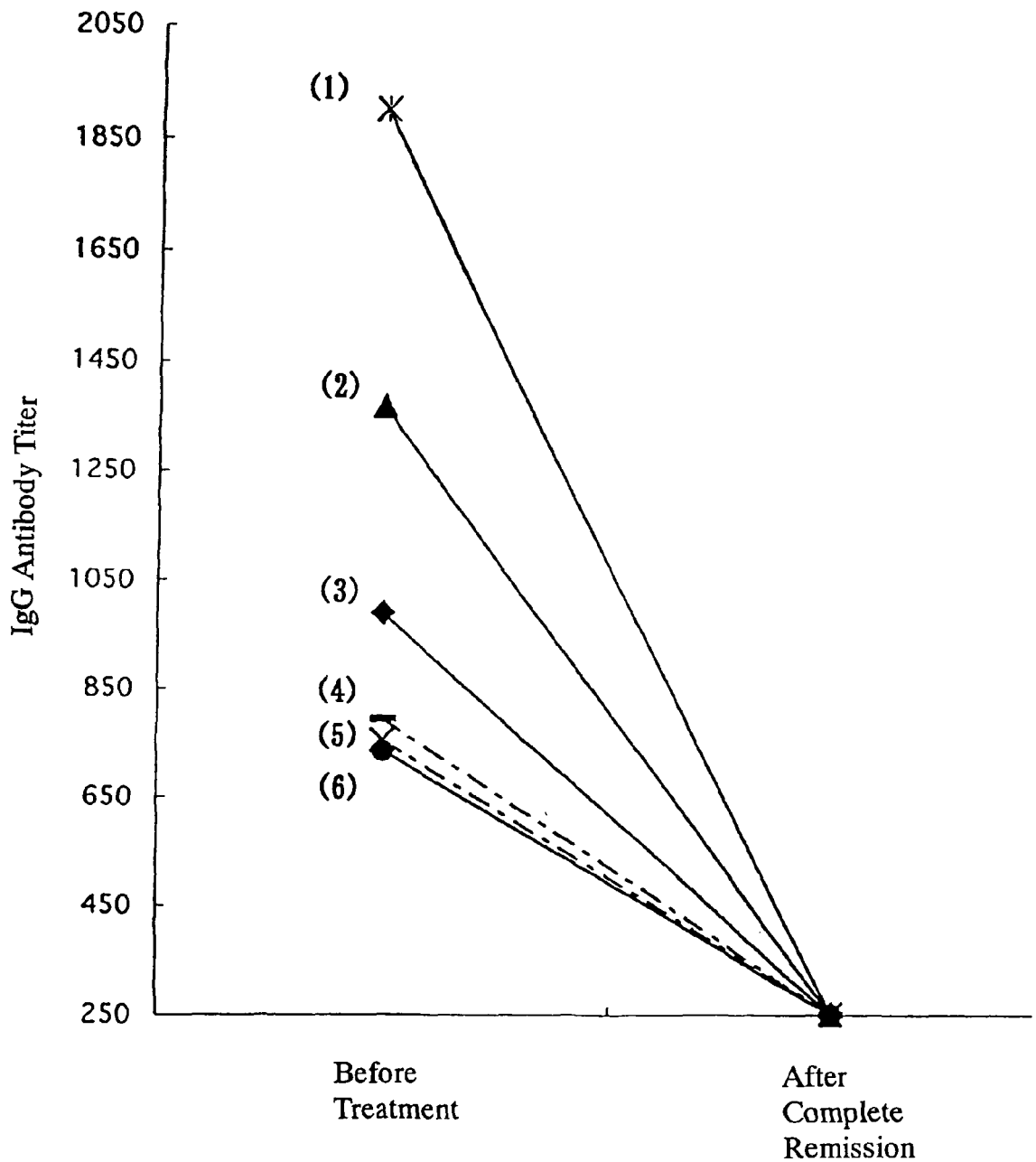
FIG. 7 is a graph showing the time course of anti-WT1 antibody titer before commencement of therapy and upon complete remission of acute leukemia as determined by the examination method of the invention in Example 3.

The results are presented in FIG. 7.

Referring to FIG. 7, the abscissa denotes before treatment and after complete remission for each patient and the ordinate denotes the anti-WT1 antibody titer of each sample. Further on the view, the lines (1)~(6) represent the respective patients with WT1-related disease, of which the solid lines mean the four patients in whom peripheral blood stem cell transplantation resulted in complete remission while the broken lines mean the two patients in whom chemotherapy resulted in complete remission.

The following can be understood from FIG. 7. Thus, the IgG anti-WT1 antibody titer detected before treatment according to the method of the invention falls definitely below the detection limit when the treatment has been effective enough to bring about complete remission (CR).

The above findings indicate that the efficacy of a treatment can be confirmed and diagnosed by following the IgG anti-WT1 antibody titer, stated differently that this titer reflects the minimal residual disease.

Example 4

Test 2 for WT1-Related Disease (1) Preparation of Samples

Sera were collected from 43 healthy adult volunteers and 46 patients with WT1-related disease (16 with myelodysplastic syndrome (MDS), 16 with acute myelocytic leukemia (AML), 7 with acute lymphocytic leukemia (ALL), and 7 with chronic myelocytic leukemia (CML)). The breakdown of the MDS patient population was: 6 with refractory anemia (RA), 4 with refractory anemia with excess of blasts (RAEB), and 6 with RAEB in transformation (RAEB-t).

The test sera were stored at −20° C. until used.

(2) Preparation of a WT1 Antigen for Determination of anti-WT1 Antibody

The DNA sequence corresponding to the WT1 fragment protein (1-294(HWT3)) was amplified by PCR in the same manner as in Example 1-(1) and cloned into the plasmid vector pET-21b(+) having the C-terminal His-Tag sequence (Novagen Inc., Madison, Wis.). The resulting plasmid was used to transfect *Escherichia coli* XL1-Blue and the transformant was examined by restriction enzyme mapping and DNA sequencing. Then, this plasmid DNA was used to transfect *Escherichia coli* BL21 (DE3) (Stratagene, La Jolla, Calif.) to prepare a recombinant DNA.

The recombinant *E. coli* BL21(DE3) was cultured till $A600=0.6$ at 37° C. and incubated in the presence of 0.1 µM IPTG for 4 hours to induce a WT1 fragment protein. The *E. coli* cells were recovered by centrifuging at 6,000 g for 10 minutes, resuspended in 4 ml (per 200 ml of culture) of buffer A (100 mM $NaH_2PO_4$, 10 mM Tris-HCl, pH 8.0) and stored at −80° C. After thawing on ice, *E. coli* was disrupted by sonication (×3, 2 min.) and centrifuged at 6,000 g for 10 minutes. The pellet containing the inclusion body was resuspended in buffer B (100 mM $NaH_2PO_4$, 10 mM Tris-HCl, pH 8.0, 300 mM NaCl, 6 M urea, 15 mM imidazole, 20 mM β-ME) and incubated on ice under mild stirring for 1 hour to denature the protein.

A column containing nickel nitro triacetic agarose (Qiagen, Hilden, Germany) was loaded with the resulting solution to let the protein be immobilized thereon. The column was washed with buffer C (the above buffer B containing 1% Tween™ but not containing β-ME) and the WT1 fragment protein was eluted with 4 ml of buffer D (the above buffer B containing 150 mM imidazole but not containing (β-ME, pH 8.0). For reholding of the recombinant protein, the eluate was placed in a cassette (SLIDE-A-LYZER dialysis cassette, Pierce Chemical Company, IL) and dialyzed against an excess of 20 mM Tris-HCl (pH 8.0) buffer at 4° C. overnight.

The recombinant protein was then concentrated with CENTRICON 30 centrifugal filter unit (Millipore Corp., Bedford, Mass.) and the protein concentration was measured by the Bradford method using a protein analysis kit (Bio-Rad Labs., Hercules, Calif.). The purity and specificity of the resulting protein was checked by SDS-PAGE and Western blot analysis and the protein was made into a 30% (v/v) glycerol solution and stored at −80° C. until used.

(3) Determination of Anti-WT1 Antibody

The WT1 fragment protein (HWT3) obtained above was conjugated to a nitrocellulose membrane (OPTITRAN, Schleicher & Schuell) at a concentration of 2.5 μg/cm2 (1-hour incubation at room temperature). This membrane was washed with PBS and, after 2 hours' blocking in 1% BSA-PBS, it was mounted on a dot-blot apparatus (Schleicher & Schuell, Dassel, Germany) according to the specification.

Determination was carried out in accordance with Example 2. Thus, 20 μl of the test serum prepared under (1) above (using PBS containing 1% BSA and 0.1% Tween 20, the serum was diluted 1/500-fold in the case of IgM or 1/2500-fold in the case of IgG) was applied to each well and incubated at room temperature for 1 hour. After washing with PBS, the membrane was reacted, in 1% BSA/PBS, with HRP-conjugated goat anti-human IgM antibody or HRP-conjugated rabbit anti-human IgG antibody at room temperature for 1 hour.

After thorough washing with PBS, the antibody titer was measured in the same manner as above. Each result was expressed in the average of at least two measurements.

Figure 8:
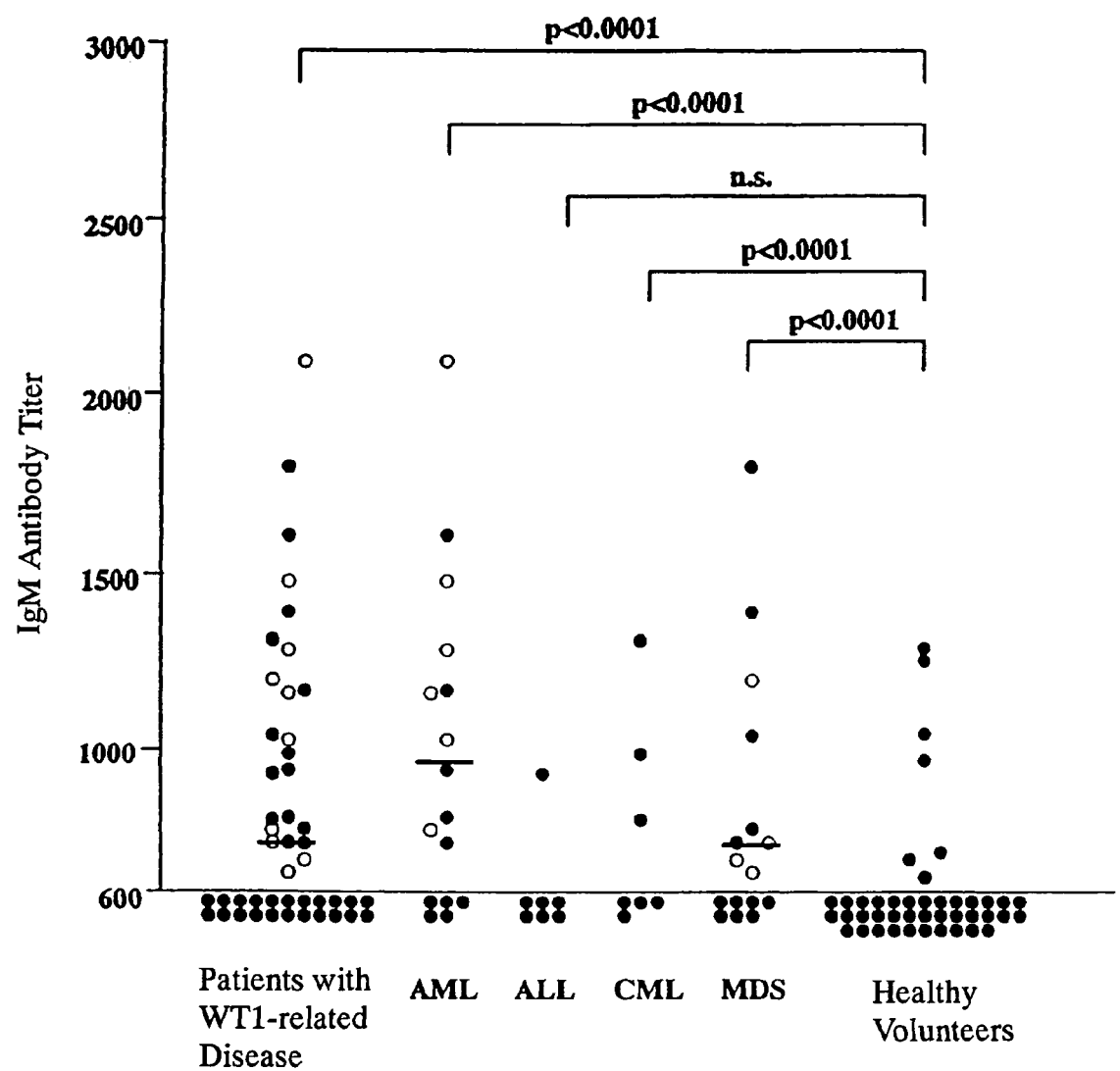
FIG. 8 is a graph showing anti-WT1 antibody titers (IgM) in WT1-related disease patients and healthy volunteers as determined by the examination method of the invention in Example 4.
Figure 9:
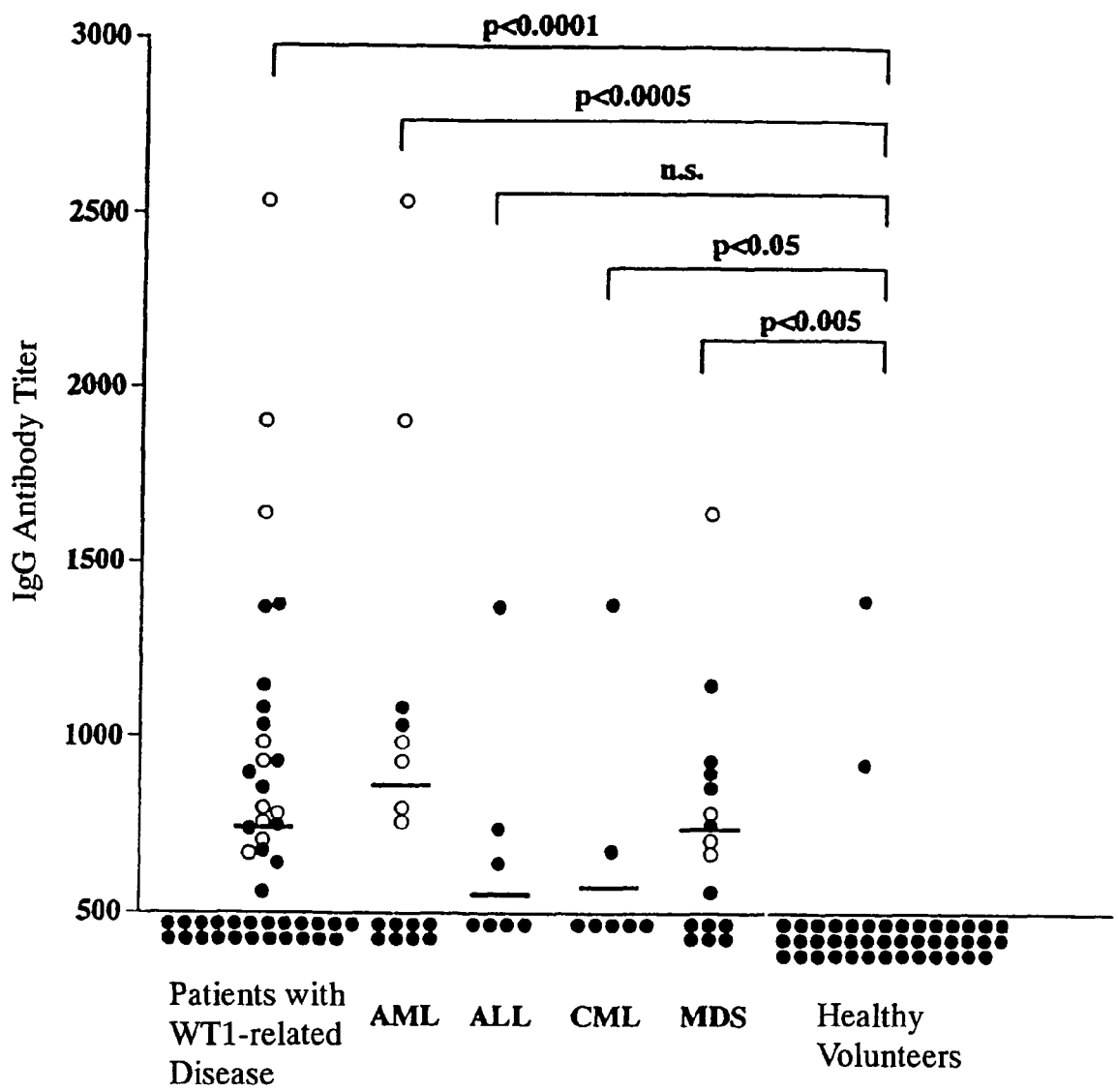
FIG. 9 is a graph showing anti-WT1 antibody titers (IgG) in WT1-related disease patients and healthy volunteers as determined by the examination method of the invention in Example 4.

(4) Results (a) The results obtained by the above method (the results of determination of IgM or IgG anti-WT1 antibody in each sample) are presented in Table 1, FIG. 8 (results of determination of IgM anti-WT1 antibody), and FIG. 9 (results of determination of IgG anti-WT1 antibody).

On each view, the ordinate represents the antibody titer (densitometric units) and the abscissa represents each sample. It should be understood that, on each view, the closed circle represents a sample containing either IgM or IgG anti-WT1 antibody alone and the open circle represents a sample containing both IgM anti-WT1 antibody and IgG anti-WT1 antibody. Further, the cut-off value used for anti-WT1 antibody was the antibody titer of 600 for IgM antibody or the antibody titer of 500 for IgG antibody (Clin. Chem., 39, 561 (1993)).

Thus, in 24 (52.2%) of 46 patients with WT1 related disease, IgM anti-WT1 antibody was detected. On the other hand, it was found in 7 (16.2%) of 43 healthy volunteers.

Compared with healthy volunteers, both the IgM anti-WT1 antibody detection rate (p=0.0001) and the IgM anti-WT1 antibody titer (p<0.0001) were significantly higher in patients with WT1-related disease.

Comparison of IgM anti-WT1 antibody titers in 4 types of WT1-related disease with the corresponding titer in healthy volunteers revealed that in patients with all types of WT1 related disease but ALL, the antibody titer was significantly higher than in healthy volunteers.

The IgG anti-WT1 antibody was detected in 23 (50.0%) of 46 patients with WT1-related disease but only in 2 (4.7%) of 43 healthy volunteers.

Compared with healthy volunteers, both the IgG anti-WT1 antibody detection rate (p=0.0001) and the IgG anti-WT1 antibody titer (p<0.0001) were significantly higher in patients with WT1-related disease. Moreover, comparison of IgG anti-WT1 antibody titers in patients with WT1 related disease with the corresponding titer in healthy volunteers revealed that in three types of the disease excepting ALL, namely AML, CML and MDS, this antibody titer was significantly high as compared with healthy volunteers.

Production of IgM and IgG anti-WT1 antibodies showed a remarkable contrast between WT1-related disease patients and healthy volunteers. Both IgM and IgG anti-WT1 antibodies were produced in 10 (21.7%) of 46 patients with WT1-related disease but none of 43 healthy volunteers had both of them. It is noteworthy that 3 patients (2 with AML and 1 with MDS) showing the highest titers of IgG anti-WT1 antibody had simultaneously produced IgM anti-WT1 antibody and that whereas 6 (37.5%) of 16 patients with AML and 4 (25.0%) of 16 patients with MDS had produced both IgM and IgG anti-WT1 antibodies, none of ALL patients and CML patients had simultaneously produced both antibodies.

No correlation was found, whether between anti-WT1 antibody titer and each of WT1 expression level (RT-PCR) and patient age or between the presence of anti-WT1 antibody and each of patient gender, condition of illness, and survival/death.

(b) In 4 leukemic patients, the anti-WT1 antibody titer was measured both at diagnosis and during continuing complete remission (CCR).

The results are presented in Table 2.

TABLE 1

|  | − | + | IgM | IgG | IgM + IgG |
|---|---|---|---|---|---|
| Healthy volunteers | 34/43 (79.1) | 9/43 (20.9) | 7/43 (16.2) | 2/43 (4.7) | 0/43 (0) |
| Patients with WT1-related disease | 9/46 (19.5) | 37/46 (80.4) | 24/46* (52.2) | 23/46* (50.0) | 10/46 (21.7) |
| AML | 3/16 (18.7) | 13/16 (81.3) | 11/16 (68.8) | 8/16 (50.0) | 6/16 (37.5) |
| ALL | 3/7 (42.9) | 4/7 (57.1) | 1/7 (14.3) | 3/7 (42.9) | 0/7 (0) |
| CML | 2/7 (28.6) | 5/7 (71.4) | 3/7 (42.9) | 2/7 (28.6) | 0/7 (0) |
| MDS | 1/16 (6.3) | 15/16 (93.7) | 9/16 (56.3) | 10/16 (62.5) | 4/16 (25.0) |

The figure in parentheses denotes a percentage (%).
The figure marked * includes the number of cases with IgM + IgG anti-WT1 antibodies.

The following can be deduced from the results presented in Table 1, FIG. 8 and FIG. 9.

TABLE 2

| Disease | AML | AML | AML | AML |
|---|---|---|---|---|
| IgM |  |  |  |  |
| at diagnosis | <600 | 772 | 1477 | 1283 |
| during CCR | 600 | 600 | <600 | <600 |
| IgG |  |  |  |  |
| at diagnosis | 989 | 794 | 754 | 1900 |
| during CCR | 500 | 500 | <500 | <500 |
| Treatment | Allo-BMT | Chemotherapy | Chemotherapy | Allo-BMT |
| Patient's condition[#] |  |  |  |  |
| Duration of CCR (yrs) | 5.5 | 5.4 | 3.9 | 3.1 |
| Immunosuppressive therapy | (—) | (—) | (—) | (—) |
| IgM | 129 (52-270)[++] | 59 | 58 | 69 |

TABLE 2-continued

| Disease | AML | AML | AML | AML |
|---|---|---|---|---|
| IgG | 1077 (880-1800) | 140 | 1120 | 1320 |
| IgA | 145 (126-517) | 120 | 150 | 1211 |

Patient's condition[#] means the condition of the patient at determination of anti-WT1 antibody titer during CCR.
[++]The figure in parenthesis denotes the normal range (mg/dl).

It is apparent from the results in Table 2 that, in all of these patients, the comparatively high anti-WT1 antibody titers found at diagnosis were no longer detected in the CCR stage. In these patients, CCR had been retained over 3.1-5.5 years, the serum IgM, IgG and IgA titers remained at the normal level, and no immunosuppressant whatever had been administered at the time of testing. These findings suggest that they had recovered fully from the immunodepressed state caused by potent chemotherapy or allogenic bone marrow transplantation. Therefore, the absence of anti-WT1 antibody in the CCR stage is considered to be the result of disappearance or alleviation of the leukemic tumorous burden and ensuing disappearance of the immunologic stimulation due to the WT1 antigen.

(c) Class Switch of anti-WT1 Antibody

IgM and IgG anti-WT1 antibodies were determined in 16 MDS patients (6 with RA, 4 with RAEB and 6 with RAEB-t). The results are presented in FIG. 10.

Figure 10:
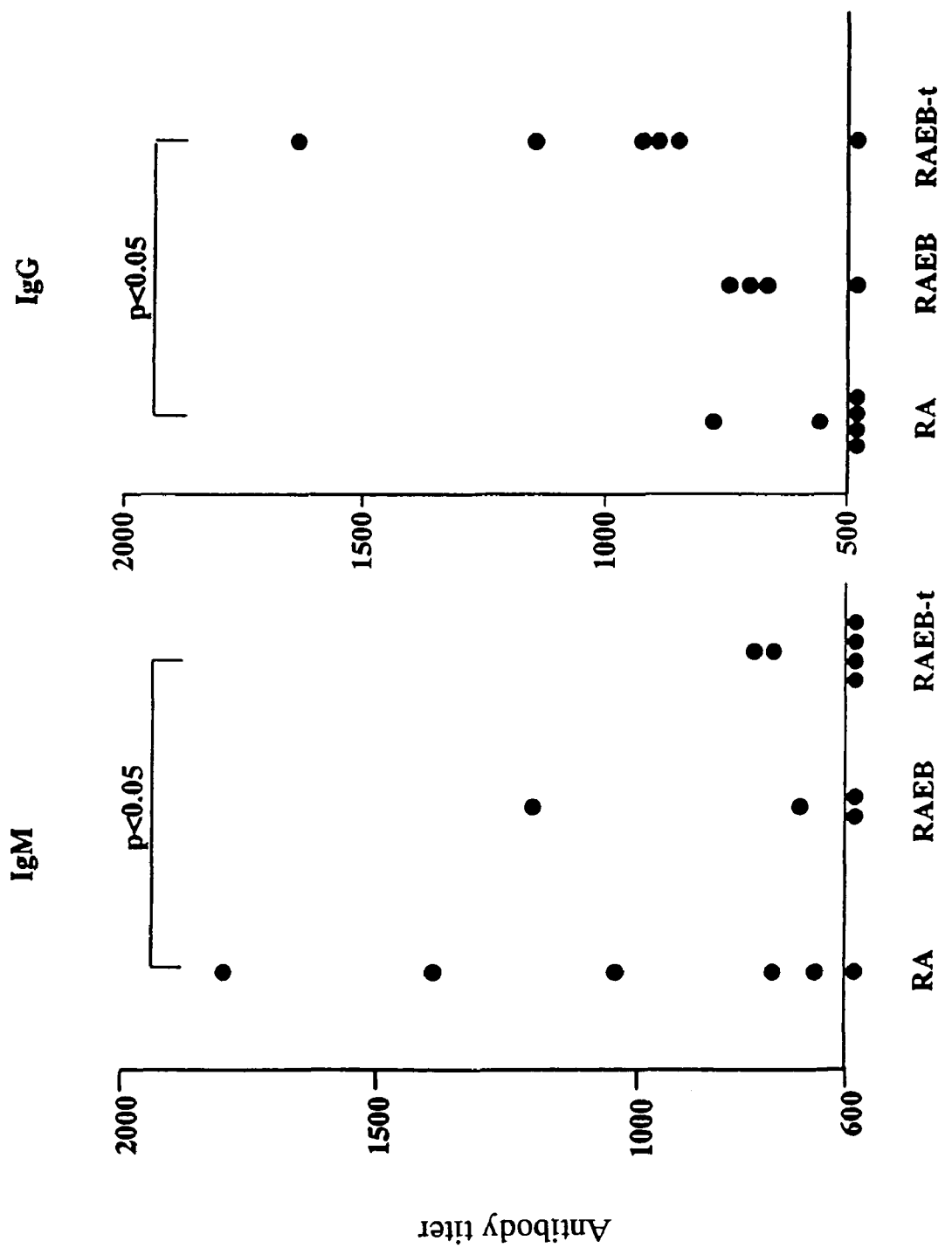
FIG. 10 is a graph showing anti-WT1 antibody titers (IgG and IgM) in WT1-related disease as determined by the examination method of the invention in Example 4.

The following can be deduced from the results shown in FIG. 10. Thus, the IgM anti-WT1 antibody was detected in 5 of 6 RA cases and comparatively high antibody titers were found in 3 of these 5 cases. In contrast, IgG anti-WT1 antibody was not detected in 4 of 6 cases and the antibody titers in the remaining 2 cases were also low.

Among RAEB patients, IgM anti-WT1 antibody and IgG anti-WT1 antibody were detected in 2 and 3, respectively, of 4 cases. The IgM anti-WT1 antibody titers were lower than those in said RA patients, while the IgG anti-WT1 antibody titers were higher.

Patients with RAEB-t were clearly different from patients with RA. Thus, low IgM anti-WT1 antibody titers were found in 2 of 6 cases, while high IgG anti-WT1 antibody titers were found in 5 of the 6 cases.

These findings suggest strongly that, in association with the progression of MDS from RA through RAEB to RAEB-t, there occurs an immunoglobulin class switch of anti-WT1 antibody from IgM to IgG.

Example 5

Test for Confirmation of the Specificity of the Anti-WT1-Antibody Assay System (5-1) To each of IgG anti-WT1 antibody-positive serum, IgG anti-WT1 antibody-negative serum, and anti-WT1 polyclonal antibody solution (S-Cruz180) was added a predetermined amount of the test protein (HWT3, albumin (HSA) or human transferrin) and the determination of anti-WT1 antibody (inhibition assay) was performed in accordance with the procedure described in Example 4.

Figure 11:
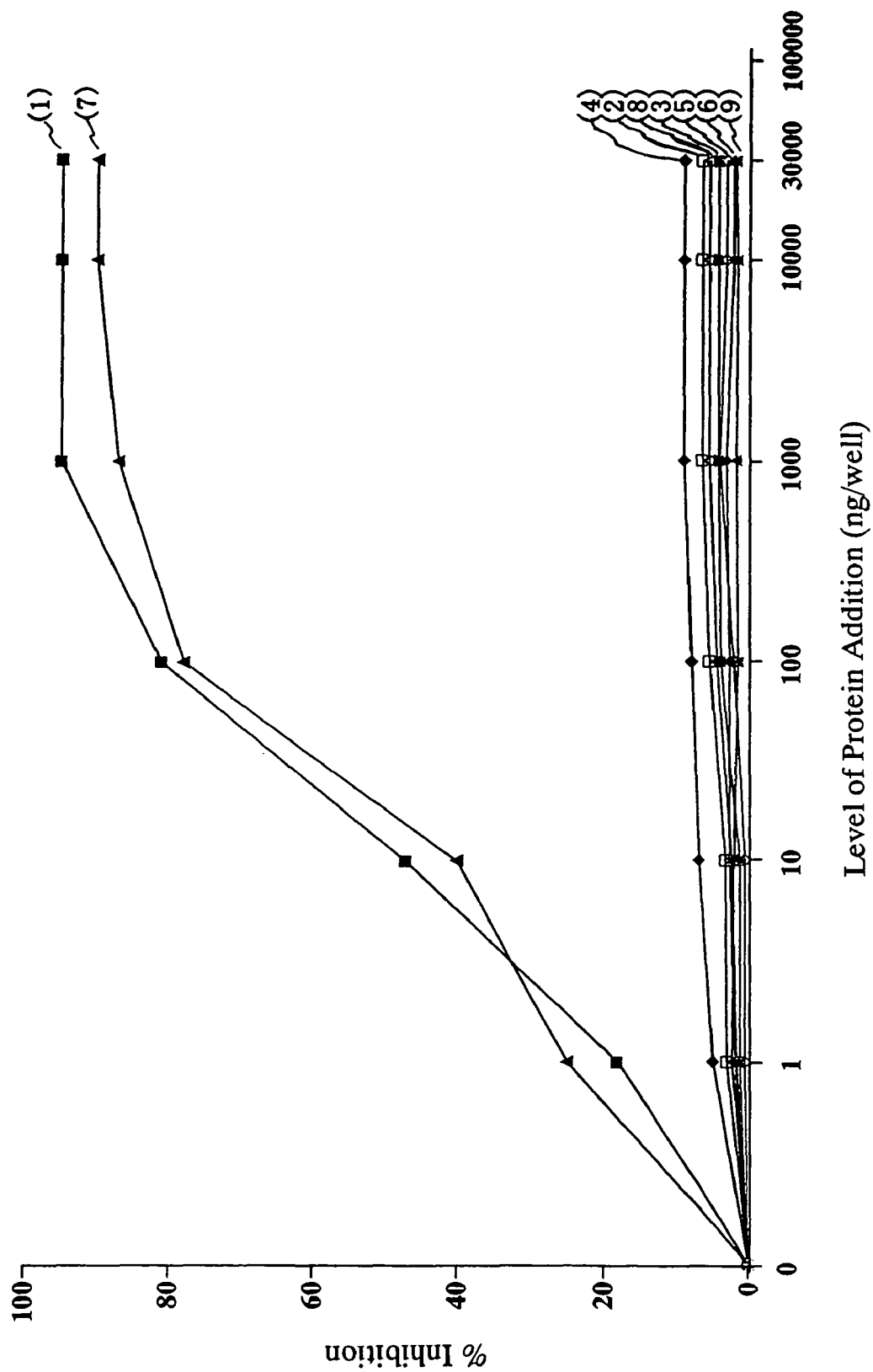
FIG. 11 is a graph showing the specificity of an anti-WT1 antibody assay system embodying the examination method of the invention as tested in Example 5-(1).

The results are presented in FIG. 11.

Referring to FIG. 11, the ordinate represents % inhibition and the abscissa represents the level of addition (ng/well) of the test protein. On the graph, (1) represents anti-WT1 antibody-positive sample+HWT3, (2) represents anti-WT1 antibody-positive sample+HSA, (3) represents anti-WT1 antibody-positive sample+transferrin, (4) represents anti-WT1 antibody-negative sample+HWT3, (5) represents anti-WT1 antibody-negative sample+HSA, (6) represents anti-WT1 antibody-negative sample+transferrin, (7) represents anti-WT1 polyclonal antibody solution+HWT3, (8) represents anti-WT1-polyclonal antibody solution+HSA, and (9) represents anti-WT1 polyclonal antibody solution+transferrin.

It is apparent from the results shown in FIG. 11 that addition of HWT3 protein, the detection system antigen, to the anti-WT1 antibody-positive sample or the anti-WT1 polyclonal antibody solution caused a varying inhibition of the detection of anti-WT1 antibody in a manner dependent on the level of addition of HWT3 protein. This HWT3 level-dependent inhibition could also be confirmed when the IgM anti-WT1 antibody-positive sample was used. On the other hand, addition of HSA or transferrin caused no such inhibition and, when the sample was anti-WT1 antibody-negative, addition of HWT3 had no influence.

These findings provided evidence that this anti-WT1 antibody assay system provides for specific detection of antibodies against WT1.

(5-2) A nuclear lysate of K562 (erythroleukemia cell line) was subjected to 10% SDS-PAGE to prepare a WT1 protein (natural WT1 protein) for Western blot analysis. Using the IgG anti-WT1 antibody-positive sample and -negative sample used in the assays performed in Example 4, Western blot analysis of the WT1 protein was carried out. The test sera were diluted 50 fold and, as the second antibody, ALP-labeled anti(rabbit or human) IgG antibody was used. As positive control, the anti-WT1 polyclonal antibody solution (S-Cruz180) was used.

Figure 12:
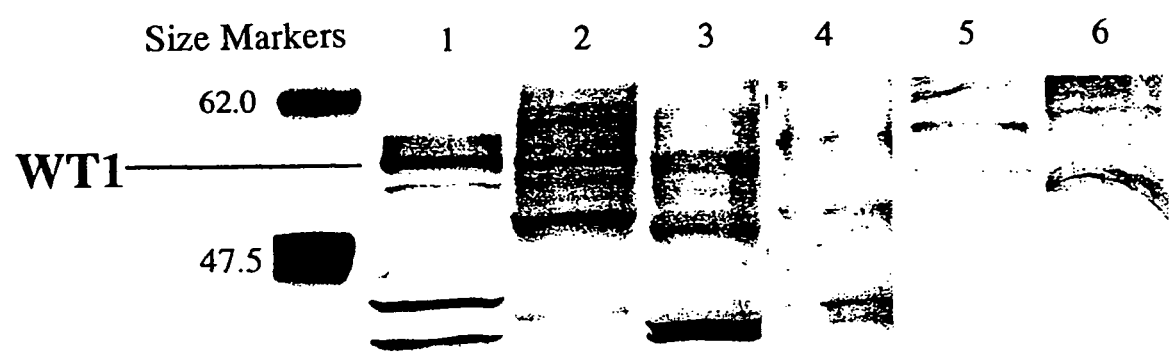
FIG. 12 is a view showing the results of a Western blot analysis made in Example 5-(2).

The results are presented in FIG. 12.

Referring to FIG. 12, the position of WT1 is shown alongside size markers in the left column.

Lane 1 represents the result with positive control (S-Cruz180), lane 2 represents the result obtained with the IgG anti-WT1 antibody-positive (ALL) sample which was assayed to have an antibody titer of 1366 in Example 4, lane 3 represents the result obtained with the IgG anti-WT1 antibody-positive (AML) sample which was assayed to have an antibody titer of 754, lane 4 represents the result obtained with the IgG anti-WT1 antibody-negative (RAEB-t) sample which was found to be below the cut-off value in Example 4, and lanes 5 and 6 represent the results obtained with IgG anti-WT1 antibody-negative healthy volunteer samples.

It is apparent from the data in FIG. 12 that natural WT1 protein can be detected with a serum found to be anti-WT1 antibody-positive (undetectable with the corresponding negative serum) in the assay system of the invention and that according to this assay system of the invention, the objective anti-WT1 antibodies recognizing natural WT1 protein can be detected.

Industrial Applicability

In accordance with the invention there is provided a novel examination method for the presence of a WT1-related disease such as leukemia, the time course of cure thereof, and the prognosis thereof. The examination method of the invention not only enables the detection and diagnosis of WT1-related diseases but also the monitoring of the progression of illness from MDS to leukemia and even the substantiation of complete remission of leukemia.

The invention claimed is:

1. A method of evaluating the progression of acute myelocytic leukemia (AML) in a patient afflicted with AML to determine whether said patient is in remission, said method comprising:
   (a) obtaining a first sample of serum of the patient;
   (b) obtaining a second sample of serum of the patient later in time;
   (c) immunoreacting a WT1 antigen with any anti-WT1 antibody present in each of said first and second samples, wherein said anti-WT1 antibody can bind to an antigen consisting of amino acids 1-294 of SEQ ID NO:5;
   (d) comparing the amount of anti-WT1 antibody present in said first sample to the amount of anti-WT1 antibody present in said second sample; and (e) determining whether the amount of anti-WT1 antibody present in the second sample is less than the amount of anti-WT1 antibody present in the first sample, and is below the detection limit;

wherein when the amount of anti-WT1 antibody present in the second sample is less than the amount of anti-WT1 antibody present in the first sample, and is below the detection limit, said patient is in complete remission.

2. The method according to claim 1, wherein said second sample is obtained after the patient is subjected to anti-AML therapy.

3. The method according to claim 1, wherein the WT1 antigen comprises amino acids 1-294 of SEQ ID NO:5.

4. The method according to claim 3, wherein the WT1 antigen is a WT1 protein lacking at least one zinc finger domain.

* * * * *

SEQUENCE LISTING

<160> NUMBER OF SEQ ID NOS: 5

<210> SEQ ID NO 1
<211> LENGTH: 27
<212> TYPE: DNA
<213> ORGANISM: Artificial Sequence
<220> FEATURE:
<223> OTHER INFORMATION: synthetic WT1 oligonucleotide primer

<400> SEQUENCE: 1
ttgaattcaa tgggctccga cgtgcgg                                    27

<210> SEQ ID NO 2
<211> LENGTH: 26
<212> TYPE: DNA
<213> ORGANISM: Artificial Sequence
<220> FEATURE:
<223> OTHER INFORMATION: synthetic WT1 oligonucleotide primer

<400> SEQUENCE: 2
ttgtcgacga agacaccgtg cgtgtg                                     26

<210> SEQ ID NO 3
<211> LENGTH: 26
<212> TYPE: DNA
<213> ORGANISM: Artificial Sequence
<220> FEATURE:
<223> OTHER INFORMATION: synthetic oligonucleotide primer HWT2

<400> SEQUENCE: 3
ttgtcgacca tgggatcctc atgctt                                     26

<210> SEQ ID NO 4
<211> LENGTH: 27
<212> TYPE: DNA
<213> ORGANISM: Artificial Sequence
<220> FEATURE:
<223> OTHER INFORMATION: synthetic oligonucleotide primer HWT4

<400> SEQUENCE: 4
ttgaattcag atccaatggg ccagcag                                    27

<210> SEQ ID NO 5
<211> LENGTH: 449
<212> TYPE: PRT
<213> ORGANISM: Homo sapiens

<400> SEQUENCE: 5

Met Gly Ser Asp Val Arg Asp Leu Asn Ala Leu Leu Pro Ala Val Pro
1               5                   10                  15

Ser Leu Gly Gly Gly Gly Gly Cys Ala Leu Pro Val Ser Gly Ala Ala
            20                  25                  30

Gln Trp Ala Pro Val Leu Asp Phe Ala Pro Pro Gly Ala Ser Ala Tyr
        35                  40                  45

Gly Ser Leu Gly Gly Pro Ala Pro Pro Ala Pro Pro Pro Pro Pro Pro
    50                  55                  60

Pro Pro Pro Pro His Ser Phe Ile Lys Gln Glu Pro Ser Trp Gly Gly
65                  70                  75                  80

Ala Glu Pro His Glu Glu Gln Cys Leu Ser Ala Phe Thr Val His Phe
                85                  90                  95

Ser Gly Gln Phe Thr Gly Thr Ala Gly Ala Cys Arg Tyr Gly Pro Phe

-continued

```
            100                 105                 110
Gly Pro Pro Pro Ser Gln Ala Ser Ser Gly Gln Ala Arg Met Phe
        115                 120                 125
Pro Asn Ala Pro Tyr Leu Pro Ser Cys Leu Glu Ser Gln Pro Ala Ile
        130                 135                 140
Arg Asn Gln Gly Tyr Ser Thr Val Thr Phe Asp Gly Thr Pro Ser Tyr
145                 150                 155                 160
Gly His Thr Pro Ser His His Ala Ala Gln Phe Pro Asn His Ser Phe
                165                 170                 175
Lys His Glu Asp Pro Met Gly Gln Gln Gly Ser Leu Gly Glu Gln Gln
            180                 185                 190
Tyr Ser Val Pro Pro Pro Val Tyr Gly Cys His Thr Pro Thr Asp Ser
        195                 200                 205
Cys Thr Gly Ser Gln Ala Leu Leu Leu Arg Thr Pro Tyr Ser Ser Asp
        210                 215                 220
Asn Leu Tyr Gln Met Thr Ser Gln Leu Glu Cys Met Thr Trp Asn Gln
225                 230                 235                 240
Met Asn Leu Gly Ala Thr Leu Lys Gly Val Ala Ala Gly Ser Ser Ser
                245                 250                 255
Ser Val Lys Trp Thr Glu Gly Gln Ser Asn His Ser Thr Gly Tyr Glu
            260                 265                 270
Ser Asp Asn His Thr Thr Pro Ile Leu Cys Gly Ala Gln Tyr Arg Ile
            275                 280                 285
His Thr His Gly Val Phe Arg Gly Ile Gln Asp Val Arg Arg Val Pro
        290                 295                 300
Gly Val Ala Pro Thr Leu Val Arg Ser Ala Ser Glu Thr Ser Glu Lys
305                 310                 315                 320
Arg Pro Phe Met Cys Ala Tyr Pro Gly Cys Asn Lys Arg Tyr Phe Lys
                325                 330                 335
Leu Ser His Leu Gln Met His Ser Arg Lys His Thr Gly Glu Lys Pro
            340                 345                 350
Tyr Gln Cys Asp Phe Lys Asp Cys Glu Arg Arg Phe Ser Arg Ser Asp
        355                 360                 365
Gln Leu Lys Arg His Gln Arg Arg His Thr Gly Val Lys Pro Phe Gln
        370                 375                 380
Cys Lys Thr Cys Gln Arg Lys Phe Ser Arg Ser Asp His Leu Lys Thr
385                 390                 395                 400
His Thr Arg Thr His Thr Gly Lys Thr Ser Glu Lys Pro Phe Ser Cys
                405                 410                 415
Arg Trp Pro Ser Cys Gln Lys Lys Phe Ala Arg Ser Asp Glu Leu Val
            420                 425                 430
Arg His His Asn Met His Gln Arg Asn Met Thr Lys Leu Gln Leu Ala
        435                 440                 445
Leu
```